US011154546B2

(12) United States Patent
Villarreal et al.

(10) Patent No.: US 11,154,546 B2
(45) Date of Patent: *Oct. 26, 2021

(54) METHODS AND COMPOSITIONS FOR TREATMENT OF MITOCHONDRIAL TOXICITY

(71) Applicant: Epirium Bio Inc., San Diego, CA (US)

(72) Inventors: Francisco Villarreal, Chula Vista, CA (US); Alan Maisel, Solana Beach, CA (US); George Schreiner, Los Altos Hills, CA (US); Guillermo M. Ceballos Reyes, Medico D.F. (MX); Pam Taub, Rancho Santa Fe, CA (US)

(73) Assignee: Epirium Bio Inc., San Diego, CA (US)

( * ) Notice: Subject to any disclaimer, the term of this patent is extended or adjusted under 35 U.S.C. 154(b) by 18 days.

This patent is subject to a terminal disclaimer.

(21) Appl. No.: 16/107,426

(22) Filed: Aug. 21, 2018

(65) Prior Publication Data
US 2019/0046517 A1 Feb. 14, 2019
US 2020/0155533 A9 May 21, 2020

Related U.S. Application Data

(63) Continuation of application No. 13/489,317, filed on Jun. 5, 2012, now Pat. No. 10,052,316.
(Continued)

(51) Int. Cl.
*A61K 31/455* (2006.01)
*A61K 36/82* (2006.01)
(Continued)

(52) U.S. Cl.
CPC .......... *A61K 31/455* (2013.01); *A61K 31/353* (2013.01); *A61K 31/573* (2013.01);
(Continued)

(58) Field of Classification Search
CPC ... A61K 31/353; A61K 31/455; A61K 31/537
See application file for complete search history.

(56) References Cited

U.S. PATENT DOCUMENTS 6,312,753 B1  11/2001  Kealey et al.
6,410,052 B1   6/2002  Morre et al.
(Continued)

FOREIGN PATENT DOCUMENTS

WO  WO2010121232 A1  10/2010
WO  2010/129138      11/2010
(Continued)

OTHER PUBLICATIONS

Barbieri, et al, "Reactive oxygen species in skeletal muscle signaling", J Signal Transuction, pp. 1-17 (2012).
(Continued)

*Primary Examiner* — San Ming R Hui
(74) *Attorney, Agent, or Firm* — Morrison & Foerster LLP

(57) ABSTRACT

The present invention relates to compositions and methods for prophylactic and/or therapeutic treatment of conditions related to mitochondrial function. In various aspects, the present invention comprises administering one or more compounds selected from the group consisting of epicatechin, an epicatechin derivative, catechin, a catechin derivative, nicorandil, and a nicorandil derivative in an amount effective to ameliorate mitochondrial toxicity caused by administration of a chemical, food, or drug.

14 Claims, 11 Drawing Sheets

Related U.S. Application Data

(60) Provisional application No. 61/493,932, filed on Jun. 6, 2011.

(51) Int. Cl.
    *A61K 45/06*     (2006.01)
    *A61K 31/353*     (2006.01)
    *A61K 31/573*     (2006.01)
    *A61K 36/185*     (2006.01)

(52) U.S. Cl.
    CPC ............ *A61K 36/185* (2013.01); *A61K 36/82* (2013.01); *A61K 45/06* (2013.01); *A61K 2300/00* (2013.01)

(56) References Cited

U.S. PATENT DOCUMENTS

| | | | |
|---|---|---|---|
| 6,528,042 B1 | 3/2003 | Brown | |
| 7,588,785 B2 | 9/2009 | Evans et al. | |
| 8,962,678 B2 | 2/2015 | Ota et al. | |
| 9,901,564 B2 | 2/2018 | Schreiner | |
| 10,052,316 B2 | 8/2018 | Villarreal | |
| 10,898,465 B2 | 1/2021 | Dugar | |
| 2002/0176898 A1 | 11/2002 | Morre | |
| 2003/0191064 A1 | 10/2003 | Kopke | |
| 2006/0111307 A1* | 5/2006 | Robbins ............... | A61K 31/137 514/27 |
| 2007/0149466 A1 | 6/2007 | Milburn et al. | |
| 2009/0047368 A1 | 2/2009 | Numata | |
| 2009/0281174 A1 | 11/2009 | Ota et al. | |
| 2009/0325906 A1 | 12/2009 | Robbins et al. | |
| 2011/0021466 A1 | 1/2011 | Villarreal | |
| 2012/0040929 A1 | 2/2012 | Courtois | |
| 2012/0095063 A1 | 4/2012 | Villareal et al. | |
| 2013/0171268 A1 | 7/2013 | Villarreal | |
| 2015/0080328 A1 | 3/2015 | Villarreal | |
| 2018/0193306 A1 | 7/2018 | Schreiner | |
| 2019/0247359 A1 | 8/2019 | Dugar | |
| 2019/0262347 A1 | 8/2019 | Dugar | |
| 2020/0390741 A1 | 12/2020 | Schreiner | |

FOREIGN PATENT DOCUMENTS

| | | |
|---|---|---|
| WO | WO2011026219 A1 | 3/2011 |
| WO | WO2013022846 A2 | 2/2013 |
| WO | 2013142816 A1 | 9/2013 |
| WO | WO2013022846 A3 | 10/2013 |
| WO | 2017221269 A1 | 12/2017 |
| WO | 2018083713 A1 | 5/2018 |
| WO | 2019164914 A1 | 8/2019 |

OTHER PUBLICATIONS

Boschi et al, "Nicorandil Analogues containing no-donor furoxans and related furazans" Bioorg. Med. Chem., vol. 8, pp. 1727-1732 (2000).
Casuso et al, "Quercetin supplementation does not enhance cerebellar mitochondrial biogenesis and oxidative status in exercised rats", Nutrition Research, vol. 35, pp. 585-591 (2015).
Dower et al, "Effects of the pure falvonoids epicatechin and quercetin on vascular function and cardiometabolic health: a randomized double-blind, placebo-controlled crossover trial", Am J Clin Nutr, pp. 1-8 (2015).
Gohil et al, "Nutrient-sensitized screening for drugs that shift energy metabolism from mitochondrial respiration to glycolysis", Nature Biotechnol. vol. 28, pp. 249-257 (2010).
Hershman, DL, et al, "Randomized double-blind placebo-controlled trial of acetyl-L-Camitine for the prevention of taxane-induced neuropathy in women undergoing adjuvant breast cancer therapy", J Clinical oncology, vol. 31, Issue 20, pp. 1-8 (2013).
Higashida K, et al, "Effects of resveratrol and SIRT1 on PGC-1 activity and mitochondrial biogenesis: a reevaluation", Plos, vol. 11, Issue 7, pp. 1-12 (2013).
Javadov S, et al, "Mitochondrial permeability transition pore opening as promising therapeutic target in cardiac diseases", J Pharmacology and experimental therapeutics, vol. 330, Issue 3, pp. 670-678 (2009).
Jenkins JS, et al, "Conversion of cortisone to cortisol and prednisone to prednisolone", Brit, Med. J., vol. 2, pp. 205-207 (1967).
Kawashima T, et al, "Constitutive SIRT1 overexpression impairs mitochondria and reduces cardiac function in mice", J Molecular and Cellular cardiology, vol. 51, pp. 1026-1036 (2011).
Kim JK, et al, "A new phenylpropanoid derivative of catechin from the needles of taxus cuspidata", Natural product research: formerly natural product letters, vol. 22, Issue 15, pp. 1365-1369 (2008).
Mingorance C, et al, "Critical update for the clinical use of L-carnitine analogs in cardiometabolic disorders", Vascular health and risk management, vol. 7, pp. 169-176 (2011).
Mitsui T, et al, "Chronic corticosteroid administration causes mitochondrial dysfunction in skeletal muscle", J Neurol, vol. 249, pp. 1004-1009 (2002).
Neustadt J, et al, "Medication-induced mitochondrial damage and disease". Mol Nutr Food Res, vol. 52, pp. 780-788 (2008).
Nielloud et al, "Emulsion properties and related know-how to attain them". Pharmaceutical emulsions and suspensions 2nd edition, pp. 1-55 (2000).
Paulsen G, et al, "Vitamin C and E supplementation hampers cellular adaptation to endurance training in humans: a double-blind randomized controlled trial", J physiol, vol. 592, Issue 8, pp. 1887-1901 (2014).
Peternelj TT, et al, "Antioxidant supplementation during exercise training", Sports med, vol. 41, Issue 12, pp. 1043-1069 (2011).
Philip A, et al, "Sirtuin1 (SIRT1) Deacetylase activity is not required for mitochondrial biogenesis or peroxisome proliferator-activated receptor-y coactivator-1a (PGC-1a) deacetylation following endurance exercise", J Biol Chem, vol. 286, Issue 35, pp. 30561-30570 (2011).
Ramirez-Sanches I, et al, "Epicatechin improves mitochondrial-related protein levels and ameliorates oxidative stress in dystrophic-sarcoglycan null mouse striated muscle", FEBS journal, vol. 281, pp. 5567-5580 (2014).
Russell, et al, "Skeletal muscle mitochondria: a major player in exercise, health and disease", Biochimica et biophysica acta, vol. 1840, pp. 1276-1284 (2014).
Schmidt M, et al, "Toxicity of green tea extracts and their constituents in rat hepatocytes in primary culture", Food and Chemical Toxicology, vol. 43, pp. 307-314 (2005).
Scholten SD, et al, "Long-term quercetin supplementation reduces lipid peroxidation but does not improve performance in endurance runners", J Sports Med, pp. 1-9 (2013).
Strobel NA, et al, "Antioxidant supplementation reduces skeletal muscle mitochondrial biogenesis", J American College of sports medicine, pp. 1-8 (2011).
Tang BL, "Sirt1 and the mitochondria", Mol Cells, vol. 39, Issue 2, pp. 87-95 (2016).
Wagner et al, "Large-scale chemical dissection of mitochondrial function", Nature Biotechnol., vol. 26, pp. 343-351 (2008).
Wagner et al, "A combination of lipoic acid plus coenzyme q10 induces PGC1, a master switch of energy metabolism, improves stress response, and increases cellular gluthathione levels in cultured C2C12 skeletal muscle cells", Oxidative Medicine and Cellular Longevity, pp. 1-10 (2012).
Abdu-Allah, H.H.M. et al. (Dec. 2005) "Synthesis of Trigonelline and Nicotinamide Linked Prodrugs of 5-Aminosalicylic Acid (5-ASA) with Analgesic and Anti-Inflammatory Effects," Bull. Pharm. Sci., Assiut. University 28(Part 2):237-253.
Chen, Y. et al. (2012). "Tacrolimus Attenuates Myocardium Damage to the Total Hepatic Ischemia-Reperfusion Via Regulation of the Mitochondrial Function," Journal of Surgical Research 172:e47-e54.
Devika, P.T. et al. (Nov. 2008, e-pub. Jun. 4, 2008). "(−)Epigallocatechingallate Protects the Mitochondria Against the Deleterious

(56) References Cited

OTHER PUBLICATIONS

Effects of Lipids, Calcium and Adenosine Triphosphate in Isoproterenol Induced Myocardial Infarcted Male Wistar Rats," Journal of Applied Toxicology 28(8):938-944.

Ha, T.K. et al. (Sep. 18, 2013, e-pub. Aug. 7, 2013). "Galangin Induces Human Colon Cancer Cell Death Via the Mitcochondrial Dysfunction and Caspase-Dependent Pathway," Experimental Biology and Medicine 238:1047-1054.

International Preliminary Report on Patentability, dated Dec. 10, 2013, for PCT Application No. PCT/US2012/040929, filed Jun. 5, 2012, 6 pages.

International Search Report, dated Aug. 17, 2012, for PCT Application No. PCT/US2012/040929, filed Jun. 5, 2012, 2 pages.

Kim, C.-H. et al. (Sep. 2008). "Epicatechin Protects Auditory Cells Against Cisplatin-Induced Death," Apoptosis 13(9):1184-1194.

Kressler, J. et al. (2011). "Quercetin and Endurance Exercise Capacity: A Systematic Review and Meta-Analysis," Applied Sciences pp. 2396-2404.

Marfe, G. et al. (2009, e-pub. Jan. 21, 2009)."Kaempferol Induces Apoptosis in Two Different Cell Lines Via Akt Inactivation, Bax and SIRT3 Activation, and Mitochondrial Dysfunction," Journal of Cellular Biochemistry 106:643-650.

Owczarek, J. et al. (2005). "Drug-Inducted Myopathies. An Overview of the Possible Mechanisms," Pharmacological Reports 57:23-34.

Pal, H.C. et al. (2013). "Fisetin Inhibits Growth, Induces G2/M Arrest and Apoptosis of Human Epidermoid Carcinoma A431 Cells: Role of Mitochondrial Membrane Potential Disruption and Consequent Caspases Activation," Experimental Dermatology 22:470-475.

Pereira, C.V. et al. (2009)."Investigating Drug-induced Mitochondrial Toxicity: A Biosensor to Increase Drug Safety?" Current Drug Safety 4(1):1-22.

Safdar, A. et al. (May 24, 2010). "Aberrant Mitochondrial Homeostasis in the Skeletal Muscle of Sedentary Older Adults," PLos One 5(5):e10778, 12 pages.

Satoh, K. et al. (Nov. 1991). "The Group at C2 of N-Ethylnicotinamide Determines the Vasodilator Potencies and Mechanisms of Action of Nicorandil and Its Congeners in Canine Coronary Arteries," Naunyn Schmiedebergs Arch Pharmacol. 344:589-595.

Tabassum, H. et al. (2007). "Catechin as an Antioxidant in Liver Mitochondrial Toxicity: Inhibition of Tamoxifen-Induced Protein Oxidation and Lipid Peroxidation," J. Biochem. Molecular Toxicology 21(3):110-117.

Tabassum, H. et al. (Oct. 1, 2008). "Catechin Abrogates Tamoxifen-Induced Liver Mitochondrial Toxicity," Toxicology Letters 180:S59, T47 Abstract.

Torrence, P.F. et al. (1993). "Synthesis and Pharmacokinetics of a Dihydropyridine Chemical Delivery System for the Antiimmunodeiciency Virus Agent Dideoxycytidine," J. Med. Chem.36:529-537.

Torres-Gonzalez, M. et al. (2012, e-pub. Apr. 1, 2012). "(−)-Epicatechin Attenuates Prednisolone Induced-Hyperglycemia," FASEB Journal 26(Suppl. 1), Abstract Only, 3 pages.

Written Opinion, dated Aug. 17, 2012, for PCT Application No. PCT/US2012/040929, filed Jun. 5, 2012, 5 pages.

Yousuf, S. et al. (2011). "Neuroprotective Effects of Tacrolimus (FK-506) and Cyclosporin (CsA) in Oxidative Injury," Brain and Behavior 1(2):87-94.

Øzbay, L.A. et al. (2011). "Cyclosporin and Tacrolimus Impair Insulin Secretion and Transcriptional Regulation in INS-1E Beta-Cells," British Journal of Pharmacology, 162:136-146.

U.S. Appl. No. 17/129,678, Dugar et al, filed Dec. 21, 2020. (Copy not submitted herewith pursuant to the waiver of 37 C.F.R. § 1.98(a)(2)(iii) issued by the Office dated Sep. 21, 2004.).

\* cited by examiner

METHODS AND COMPOSITIONS FOR TREATMENT OF MITOCHONDRIAL TOXICITY

CROSS REFERENCE TO RELATED APPLICATIONS

The present application claims priority to U.S. Provisional Patent Application No. 61/493,932 filed Jun. 6, 2011, which is hereby incorporated in its entirety including all tables, figures, and claims.

BACKGROUND

The following discussion of the background of the invention is merely provided to aid the reader in understanding the invention and is not admitted to describe or constitute prior art to the present invention.

The present patent application relates to treatment and prevention of acute injuries, and prevention or reversal of states of chronic mitochondrial depletion or dysfunction.

Mitochondria are specialized compartments present in cells that are responsible for creating more than 90% of the energy needed by the body to sustain life and support growth. When mitochondrial function fails, less energy is generated within the cell. Cell injury and ultimately cell death follow. A number of drug classes have recently been identified as inducing organ degeneration or other side effects which are mediated by their effects on mitochondrial bioenergetics. The most frequent targets in drug-induced mitochondrial dysfunction are the heart, liver and kidneys, although other organs can also be affected. A recent summary by Pereira et al. in *Current Drug Safety*, 4: 34-54, 2009 (hereby incorporated by reference in its entirety) includes the following non-limiting list of exemplary drugs and drug classes:

1. Cardiovascular Toxicity

Nucleoside reverse transcriptase inhibitors (NRTIs); Zidovudine (AZT); Bupivacaine; Lidocaine; Thiazolidinediones (TZD); Doxorubicin (DOX); Sorafenib; Daunorubicin; Epirubicin; Idarubicin; Celecoxib; Diclofenac; Ibuprofen; Indomethacin; Mefenamic acid; Meloxicam; Naproxen; Piroxicam; Sulindac; Atenolol; Pioglitazone; Rosiglitazone 2. Hepatic Toxicity Isoniazid; Valproic acid; Tamoxifen; Flutamide; Lamivudine; Zidovudine (AZT); Zalcitabine; Phenoformin; Metformin; Nefazodone; Abacavir; Didanosine; Nevirapine; Tenofovir; Stavudine; Ketoconazole; Divalproex Sodium 3. Renal Toxicity Doxorubicin (DOX); Cysplatin; Gentamicin; Cyclosporin A; Ifosfamide; Statins; Tenofovir This understanding is also discussed in detail in Gohil et al., *Nature Biotechnol.* 28: 249-257, 2010; and Wagner et al., and *Nature Biotechnol.* 26: 343-351, 2008, each of which is hereby incorporated by reference in its entirety. Reflecting this understanding, the phrase "mitochondrial toxicity" as used herein refers to failure of the mitochondria resulting from the administration of chemical compositions to a subject. The manifestations of mitochondrial toxicity can be quite varied, due to the different functions carried out by the mitochondria. These functions include:

Oxidative phosphorylation, in which substrates are oxidized by the enzymes of the mitochondrial respiratory chain in order to establish an electrochemical gradient of protons across the mitochondrial membrane. This potential is used by ATP synthase to produce ATP, the energy currency of the body;

Citric acid cycle, the reactions of which occur inside the mitochondrial matrix and which lead to the production to NADH and succinate under aerobic conditions; and Calcium homeostasis and the permeability transition pore. Calcium concentrations inside the mitochondrial matrix depend not only of an electrogenic mitochondrial calcium uniporter (MCU) but also on antiporters (Na+/Ca2+ and H+/Ca2+). Inside mitochondria, calcium modulates the activity of several important enzymes. An excess of calcium accumulation in the matrix leads to the formation of the mitochondrial permeability transition pore, which spans the inner and outer mitochondrial membrane and whose opening leads to the collapse of the transmembrane electric potential, ultimately leading to mitochondrial and cellular dysfunction.

Given these varied functions, it is perhaps not surprising that mitochondria can be affected by chemical exposure at various levels. These include uncoupling of oxidative phosphorylation, inhibition of key enzymes, inhibition of fatty acid metabolism, effecting permeability pores, inducement of apoptosis, inhibition of mitochondrial protein synthesis, and/or reduction in total mitochondrial numbers.

There remains a need in the art for prophylactic and therapeutic approaches for the treatment of mitochondrial toxicity.

SUMMARY

It is an object of the invention to provide compositions and methods for prophylactic and/or therapeutic treatment of mitochondrial toxicity. In various aspects described hereinafter, the present invention comprises administering one or more compounds selected from the group consisting of epicatechin, an epicatechin derivative, catechin, a catechin derivative, nicorandil, and a nicorandil derivative in an amount effective to stimulate mitochondrial function in cells. Stimulation of mitochondrial function in cells may comprise stimulation of one or more of mitochondrial respiration and mitochondrial biogenesis. The methods and compositions described herein can assist in prevention of impaired mitochondria function and biogenesis and thus prevention of the consequences of impaired mitochondrial biogenesis resulting from administration of chemical compositions that exhibit mitochondrial toxicity.

In a first aspect, the present invention provides methods for preventing or treating adverse events associated with the use of chemical compositions such as approved medications in which the adverse event is caused by, or associated with, perturbations in mitochondrial number, function or structure. The methods comprise administering to a subject in need thereof one or more compounds selected from the group consisting of epicatechin, an epicatechin derivative, catechin, a catechin derivative, nicorandil, and a nicorandil derivative, and pharmaceutically acceptable salts and prodrugs thereof. Preferably the method reduces symptoms of mitochondrial toxicity due to the subject's exposure to chemical compositions that exhibit mitochondrial toxicity.

In certain embodiments, the one or more compounds selected from the group consisting of epicatechin, an epicatechin derivative, catechin, a catechin derivative, nicorandil, and a nicorandil derivative, and pharmaceutically acceptable salts and prodrugs thereof are administered in combination with one or more chemical compositions which exhibit mitochondrial toxicity. Such chemical compositions include, but are not limited to, those described above in regard to drug-induced mitochondrial dysfunction of the heart, liver and kidneys.

In preferred embodiments, the chemical composition that exhibits mitochondrial toxicity is identified based on the demonstration of one or more biological effects indicative of mitochondrial toxicity by the chemical composition. Such effects include, but are not limited to, abnormal mitochondrial respiration, abnormal oxygen consumption, abnormal extracellular acidification rate, abnormal mitochondrial number, abnormal lactate accumulation, abnormal ATP levels, etc.

In certain embodiments, the subject is selected for receipt of the one or more compounds selected from the group consisting of epicatechin, an epicatechin derivative, catechin, a catechin derivative, nicorandil, and a nicorandil derivative, and pharmaceutically acceptable salts and prodrugs thereof based on the occurrence of one or more physiological manifestations of mitochondrial toxicity in the subject. Such manifestations include, but are not limited to, elevations in markers known to relate to injury to the heart, liver, and/or kidney. Examples include elevated serum liver enzymes, elevated cardiac enzymes, lactic acidosis, elevated blood glucose, elevated serum creatinine, etc. This list is not meant to be limiting.

The one or more compounds selected from the group consisting of epicatechin, an epicatechin derivative, catechin, a catechin derivative, nicorandil, and a nicorandil derivative, and pharmaceutically acceptable salts and prodrugs thereof are administered in an "effective amount." This term is defined hereinafter. Unless dictated otherwise, explicitly or otherwise, an "effective amount" is not limited to a minimal amount sufficient to ameliorate a condition, or to an amount that results in an optimal or a maximal amelioration of the condition. In the case when two or more compounds are administered together, an effective amount of one such compound may not be, in and of itself, be an effective amount, but may be an effective amount when used together with additional compounds.

Preferably, the effective amount is an amount which stimulates mitochondrial function in cells. Such stimulation of mitochondrial function in cells may comprise stimulation of one or more of mitochondrial respiration and mitochondrial biogenesis. The methods and compositions described herein can assist in prevention of the consequences of mitochondrial toxicity which has not yet occurred, as well as provide for the active therapy of mitochondrial toxicity that may have already occurred.

In certain embodiments, the administration of compound(s) comprises administering at least 0.1 µM catechin, a catechin derivative, epicatechin or an epicatechin derivative to cells, at least 0.25 µM catechin, a catechin derivative, epicatechin or an epicatechin derivative, at least 0.5 µM catechin, a catechin derivative, epicatechin or an epicatechin derivative, and at least 1 µM catechin, a catechin derivative, epicatechin or an epicatechin derivative. In various embodiments, at least the desired concentration is maintained for at least 30 minutes, 1 hour, 3 hours, 6 hours, 12 hours, 24 hours, 48 hours, 72 hours, or more. In various other embodiments, at least the desired concentration is achieved at least once during each 12 hour period over at least 24 hours, 48 hours, 72 hours, 1 week, one month, or more; or at least once during each 24 hour period over at least 48 hours, 72 hours, 1 week, one month, or more. In order to maintain a desired concentration for a desired time, multiple doses of one or more compounds may be employed.

The dosing interval may be determined based on the T1/2 for the clearances of each compound of interest from the body.

One or more compounds selected from the group consisting of epicatechin, an epicatechin derivative, catechin, a catechin derivative, nicorandil, and a nicorandil derivative may be delivered to an animal by a parenteral or enteral route in an amount effective to stimulate mitochondrial function in cells of said animal. Preferred enteral routes of administration include delivery by mouth (oral), nasal, rectal, and vaginal routes. Preferred parenteral routes of administration include intravenous, intramuscular, subcutaneous, and intraperitoneal routes. When more than one compound is being administered, each need not be administered by the same route. Moreover, one or more such compounds can be administered in sustained release formulation as described in U.S. Pat. No. 6,410,052, which is hereby incorporated by reference.

In those methods in which epicatechin, an epicatechin derivative, catechin, or a catechin derivative is delivered, it is preferred that the selected compound be at least 90% pure relative to other compounds selected from the group consisting of epicatechin, an epicatechin derivative, catechin, or a catechin derivative. For example, if the compound is epicatechin, it contains no more than 10% contamination with epicatechin derivatives, catechin, and catechin derivatives. More preferably the selected epicatechin, epicatechin derivative, catechin, or catechin derivative is at least 95% pure relative to other compounds selected from the group consisting of epicatechin, an epicatechin derivative, catechin, or a catechin derivative. It is noted that this does not exclude, however combination with nicorandil or a nicorandil derivative in substantial concentration. Thus in certain embodiments an epicatechin, an epicatechin derivative, catechin, or a catechin derivative is delivered in combination with nicorandil or a nicorandil derivative in the present methods. These are preferably provided in a single pharmaceutical composition.

While the phrase "administered together" as used herein may refer to the provision of chemical compositions in the same pharmaceutical composition, the phrase as used herein is not intended to imply that this must be so. Rather, two or more chemical compositions are "administered together" if the $T_{1{\scriptstyle /}2}$ for the clearances of each composition from the body overlaps at least partially with one another. For example, if a first pharmaceutical has a $T_{1{\scriptstyle /}2}$ for clearance of 1 hour and is administered at time=0, and a second pharmaceutical has a $T_{1{\scriptstyle /}2}$ for clearance of 1 hour and is administered at time=45 minutes, such pharmaceuticals are considered administered together. Conversely, if the second drug is administered at time=2 hours, such pharmaceuticals are not considered administered together.

The term "epicatechin derivative" as used herein refers to any compound which retains the ring structure and 3R(−) stereochemistry of epicatechin itself, but which contains one or more substituent groups relative to epicatechin. Certain naturally occurring epicatechin derivatives are known, such as (−)-epigallocatechin (EGC), (−)-epicatechin-3-gallate (ECG) and (−)-epigallocatechin-3-gallate (EGCG). The term also includes combination molecules or prodrugs which release epicatechin or a derivative thereof when administered to a subject. Such a combination molecule may include, for example, epicatechin and nicorandil joined by a hydrolysable linger group. Similarly, the term "catechin derivative" as used herein refers to any compound which retains the ring structure and 3R(+) stereochemistry of catechin itself, but which contains one or more substituent groups relative to catechin. These may be formulated for parenteral or enteral routes of administration.

Epicatechin, catechin, and their derivatives may be made synthetically, or may be isolated from natural sources which contain these molecules, such as chocolate, tea, and nuts. The term "chocolate" refers to a solid or semi-plastic food and is intended to refer to all chocolate or chocolate-like compositions containing a dispersion of solids within a fat phase. The term is intended to include compositions conforming to the U.S. Standards of Identity (SOD, CODEX *Alimentarius* and/or other international standards and compositions not conforming to the U.S. Standards of Identity or other international standards. The term includes sweet chocolate, bittersweet or semisweet chocolate, milk chocolate, buttermilk chocolate, skim milk chocolate, mixed dairy product chocolate, sweet cocoa and vegetable fat coating, sweet chocolate and vegetable fat coating, milk chocolate and vegetable fat coating, vegetable fat based coating, pastels including white chocolate or coating made with cocoa butter or vegetable fat or a combination of these, nutritionally modified chocolate-like compositions (chocolates or coatings made with reduced calorie ingredients) and low fat chocolates, unless specifically identified otherwise. See, e.g., U.S. Pat. No. 6,312,753, which is hereby incorporated by reference herein. By way of example, epicatechin, catechin, and their derivatives may be delivered by administration of tea extracts, cocoa components, partially and fully defatted cocoa solids, cocoa nibs and fractions derived therefrom, cocoa polyphenol extracts, cocoa butter, chocolate liquors, and mixtures thereof.

The term "nicorandil derivative" as used herein refers to any compound which retains the N-ethyl C-2 nitroxy moiety of N-[2-(Nitroxy)ethyl]-3-pyridinecarboxamide (nicorandil), but which contains one or more substituent groups relative to nicorandil. Examples include those disclosed in Boschi et al., Bioorg. Med. Chem. 8: 1727-32, 2000; and Satoh et al., Naunyn Schmiedebergs Arch Pharmacol. 344: 589-95, 1991. The term also includes combination molecules or prodrugs which release nicorandil or a derivative thereof when administered to a subject. Such a combination molecule may include, for example, epicatechin and nicorandil joined by a hydrolysable linger group.

The compounds and derivatives discussed above may be formulated as pharmaceutical compositions comprising a derivative or pharmaceutically acceptable salt described herein and a pharmaceutically acceptable excipient. These may be formulated for parenteral or enteral routes of administration. The compounds and derivatives discussed above may also be formulated as nutraceutical compositions as described hereinafter.

The details of one or more embodiments of the disclosure are set forth in the accompanying drawings and the description below. Other features, objects, and advantages of the disclosure will be apparent from the description and drawings, and from the claims.

DETAILED DESCRIPTION

Figure 1:
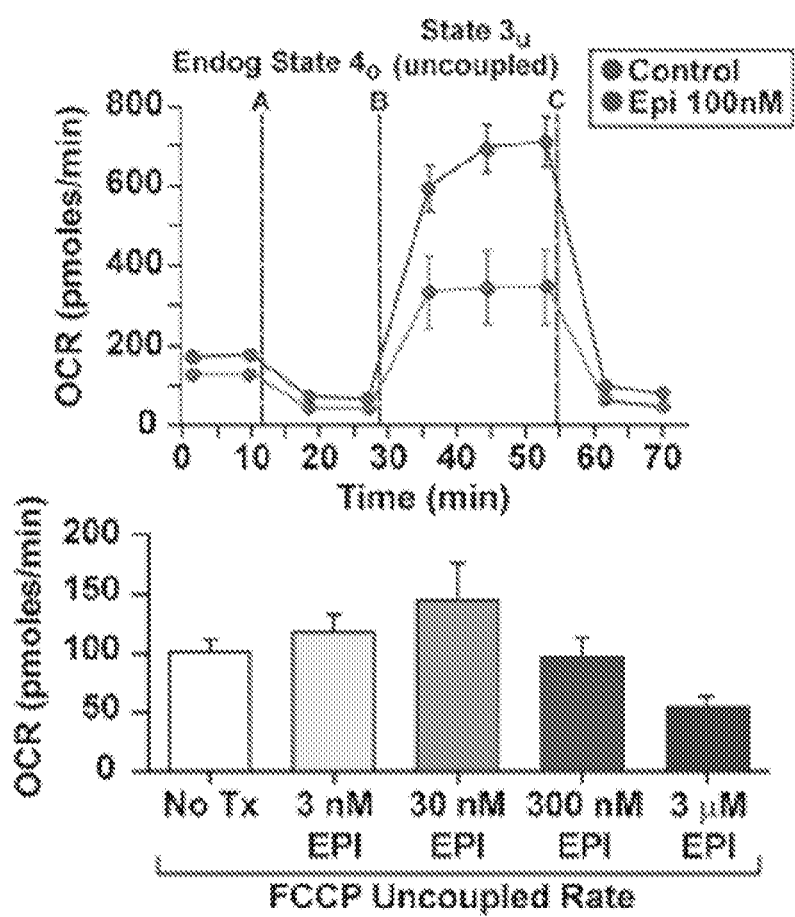
FIG. 1 depicts epicatechin stimulation on-demand mitochondrial respiration in human cells.

Unless specifically noted otherwise herein, the definitions of the terms used are standard definitions used in the art of pharmaceutical sciences. As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the disclosure. Nothing herein is to be construed as an admission that the inventors are not entitled to antedate such disclosure by virtue of prior disclosure.

The present disclosure provides a method for prophylaxis and/or treatment of, and/or ameliorating the symptoms of, a condition related to mitochondrial function in a mammalian subject caused by one or more chemical compositions which cause mitochondrial toxicity. The methods described herein comprise administering to the subject an effective amount one or more compounds selected from the group consisting of epicatechin, an epicatechin derivative, catechin, a catechin derivative, nicorandil, and a nicorandil derivative, and pharmaceutically acceptable salts and prodrugs thereof.

Mechanisms that perturb mitochondrial function or number can be broadly divided into three categories: (1) modulation of mitochondrial metabolism; (2) injury to the mitochondria such that structural damage or alteration inhibits the important functions of mitochondria such as oxidative phosphorylation or calcium sequestration; and (3) decreased number of mitochondria arising from persistent or extreme injury to the mitochondria and resulting in sustained impairment of mitochondrial function in the absence of biogenesis. Chronic mitochondrial depletion and the symptoms arising thereof can occur as a result of drug-associated toxicity or as a combination of drug associated toxicity occurring within a background of biological depletion of mitochondrial number, as occurs in diabetes, obesity, and during the course of aging.

Examples of drugs whose adverse side effects are associated with perturbation of mitochondrial number, function or structure: nucleoside reverse transcriptase inhibitors, zidovudine, bupivacaine, lidocaine, thiazolidinediones, doxorubicin, sorafenib, daunorubicin, epirubicin, idarubicin, celecoxib, diclofenac, ibuprofen, indomethacin, mefenamic acid, meloxicam, naproxen, piroxicam, sulindac, atenolol, pioglitazone, rosiglitazone, isoniazid, valproic acid, tamoxifen, flutamide, lamivudine, zalcitabine, phenformin, metformin, nefazodone, abacavir, didanosine, nevirapine, tenofovir, stavudine, ketoconazole, divalproex sodium, cysplatin, gentamicin, a cyclosporin, ifosfamide, a statin, and tenofovir, metformin, corticosteroids including cortisol and predisone and dexamethasone and triamcinalone and prednisolone, inotropes such as epinephrine, isoproterenol, and other compounds that augment myocardial contractility, fibrates as a class, including clofibrate, gemfibrizole, cyprofibrate, and bezafibrate. This list is not intended as a complete or restricted list, but simply serves as examples of a significant complication of taking drugs approved for therapeutic purposes, in which mitochondrial toxicity results in adverse events experienced by patients taking such medicines, sometime to the point of being unable to remain on the medicines or being unable to take the medicines at an optimal dose. In this instance, perturbing effects on mitochondrial function or number are not part of the intended therapeutic mechanism of these drugs, but rather are an unintended side effect of such drugs, limiting their therapeutic usefulness because of the side effects adversely affecting mitochondria, the predominant energy source for effective cellular function. Individuals at risk for a condition related to mitochondrial toxicity can decrease the risk of such toxicity in future events prophylactically. In the event that there is a present condition related to mitochondrial toxicity, it is contemplated that the therapeutic administration of the compositions of the present invention will reduce symptoms from such condition.

Epicatechin, catechin, nicorandil, or derivatives or salts thereof can be formulated as disclosed herein or its presence otherwise can be created or increased, in combination chemical compositions which exhibit mitochondrial toxicity. By way of example, a single pharmaceutical composition may comprise an effective amount of one or more compounds selected from the group consisting of epicatechin, an epicatechin derivative, catechin, a catechin derivative, nicorandil, and a nicorandil derivative, and pharmaceutically acceptable salts and prodrugs thereof, together with an effective amount of one or more compounds selected from the group consisting of a nucleoside reverse transcriptase inhibitor, zidovudine, bupivacaine, lidocaine, thiazolidinediones, doxorubicin, sorafenib, daunorubicin, epirubicin, idarubicin, celecoxib, diclofenac, ibuprofen, indomethacin, mefenamic acid, meloxicam, naproxen, piroxicam, sulindac, atenolol, pioglitazone, rosiglitazone, isoniazid, valproic acid, tamoxifen, flutamide, lamivudine, zalcitabine, phenformin, metformin, nefazodone, abacavir, didanosine, nevirapine, tenofovir, stavudine, ketoconazole, divalproex sodium, cysplatin, gentamicin, a cyclosporin, ifosfamide, a statin, and tenofovir.

Alternatively, an effective amount of one or more compounds selected from the group consisting of epicatechin, an epicatechin derivative, catechin, a catechin derivative, nicorandil, and a nicorandil derivative, and pharmaceutically acceptable salts and prodrugs thereof, may be given to an individual as a separate pharmaceutical from one or more compounds selected from the group consisting of a nucleoside reverse transcriptase inhibitor, zidovudine, bupivacaine, lidocaine, thiazolidinediones, doxorubicin, sorafenib, daunorubicin, epirubicin, idarubicin, celecoxib, diclofenac, ibuprofen, indomethacin, mefenamic acid, meloxicam, naproxen, piroxicam, sulindac, atenolol, pioglitazone, rosiglitazone, isoniazid, valproic acid, tamoxifen, flutamide, lamivudine, zalcitabine, phenformin, metformin, nefazodone, abacavir, didanosine, nevirapine, tenofovir, stavudine, ketoconazole, divalproex sodium, cysplatin, gentamicin, a cyclosporin, ifosfamide, a statin, and tenofovir.

In one variation of any of the embodiments or aspects disclosed herein a compound selected from the group consisting of epicatechin, derivatives thereof and pharmaceutically acceptable salts thereof is administered. In another variation of any of the embodiments or aspects disclosed herein epicatechin or a pharmaceutically acceptable salt thereof is administered. The epicatechin, its derivative or its salt administered via the means disclosed herein can be in any variety of concentrations, combination with other elements or agents, temperatures or other states best suited for the targeted applications.

Compounds of the disclosure are preferably administered orally in a total daily dose of about 0.1 mg/kg/dose to about 100 mg/kg/dose, alternately from about 0.3 mg/kg/dose to about 30 mg/kg/dose. In another embodiment the dose range is from about 0.5 to about 10 mg/kg/day. Alternately about 0.5 to about 1 mg/kg/day is administered. Generally between about 25 mg and about 1 gram per day can be administered; alternately between about 25 mg and about 200 mg can be administered. The use of time-release preparations to control the rate of release of the active ingredient may be preferred. The dose may be administered in as many divided doses as is convenient. Such rates are easily maintained when these compounds are intravenously administered as discussed below.

For the purposes of this disclosure, the compounds may be administered by a variety of means including orally, parenterally, by inhalation spray, topically, or rectally in formulations containing pharmaceutically acceptable carriers, adjuvants and vehicles. The term parenteral as used here includes but is not limited to subcutaneous, intravenous, intramuscular, intraarterial, intradermal, intrathecal and epidural injections with a variety of infusion techniques. Intraarterial and intravenous injection as used herein includes administration through catheters. Administration via intracoronary stents and intracoronary reservoirs is also contemplated. The term oral as used herein includes, but is not limited to sublingual and buccal. Oral administration includes fluid drinks, energy bars, as well as pill formulations.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents; such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the disclosure contain the active materials in admixture with excipients suitable for the manufacture of aqueous-suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as *arachis* oil, olive oil, sesame oil or coconut oil, or a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the disclosure suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the disclosure may also be in the form of oil-in-water emulsions. The oily phase may be a vegetable oil, such as olive oil or *arachis* oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the disclosure may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain 0.07 to 1.7 mmol (approximately 20 to 500 mg) of active material compounded with an appropriate and convenient amount of carrier material-which may vary from about 5 to about 95% of the total compositions. It is preferred that the pharmaceutical composition be prepared which provides easily measurable amounts for administration.

As noted above, formulations of the disclosure suitable for oral administration may be presented as discrete units such as capsules, cachets or tablets each containing a predetermined amount of the active ingredient, as a powder or granules; as a solution or a suspension in an aqueous or non-aqueous liquid, or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropyl ethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide. slow or controlled release of the active ingredient therein using, for example, hydroxypropyl methylcellulose in varying proportions to provide the desired release profile. Tablets may optionally be provided with an enteric coating, to provide release in parts of the gut other than the stomach. This is particularly advantageous with the compounds of formula 1 when such compounds are susceptible to acid hydrolysis.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

As used herein, pharmaceutically acceptable salts include, but are not limited to: acetate, pyridine, ammonium, piperazine, diethylamine, nicotinamide, formic, urea, sodium, potassium, calcium, magnesium, zinc, lithium, cinnamic, methylamino, methanesulfonic, picric, tartaric, triethylamino, dimethylamino, and tris(hydroxymethyl)aminomethane. Additional pharmaceutically acceptable salts are known to those skilled in the art.

As used herein, the term "effective amount" means the amount of a composition useful for causing a desired biological effect. In the case of compositions such as nucleoside reverse transcriptase inhibitors, zidovudine, bupivacaine, lidocaine, thiazolidinediones, doxorubicin, sorafenib, daunorubicin, epirubicin, idarubicin, celecoxib, diclofenac, ibuprofen, indomethacin, mefenamic acid, meloxicam, naproxen, piroxicam, sulindac, atenolol, pioglitazone, rosiglitazone, isoniazid, valproic acid, tamoxifen, flutamide, lamivudine, zalcitabine, phenoformin, metformin, nefazodone, abacavir, didanosine, nevirapine, tenofovir, stavudine, ketoconazole, divalproex sodium, cysplatin, gentamicin, cyclosporins, ifosfamide, statins, tenofovir, etc., these effective amounts are well known in the art. In the case of the use of epicatechin, an epicatechin derivative, catechin, a catechin derivative, nicorandil, or a nicorandil derivative for ameliorating the mitochondrial toxicity of such drugs, useful plasma concentrations can be readily determined by the skilled artisan.

An effective amount to be administered systemically depends on the body weight of the subject. Typically, an effective amount to be administered systemically is about 0.1 mg/kg to about 100 mg/kg and depends upon a number of factors including, for example, the age and weight of the subject (e.g., a mammal such as a human), the precise condition requiring treatment and its severity, the route of administration, and will ultimately be at the discretion of the attendant physician or veterinarian.

The term "ameliorate" as used herein refers to prophylactically or therapeutically reducing a desired symptom, condition, or disease. This term can include the ability to increase the duration of treatment, wherein the duration of treatment with the chemical composition which causes mitochondrial toxicity would otherwise be limited by its toxicity; or the ability to administer an increased concentration of the chemical composition which causes mitochondrial toxicity would otherwise be limited by its toxicity.

The compositions of the present invention may also be formulated as neutraceutical compositions. The term "nutraceutical composition" as used herein refers to a food product, foodstuff, dietary supplement, nutritional supplement or a supplement composition for a food product or a foodstuff comprising exogenously added catechin and/or epicatechin. Details on techniques for formulation and administration of such compositions may be found in Remington, The Science and Practice of Pharmacy 21st Edition (Mack Publishing Co., Easton, Pa.) and Nielloud and Marti-Mestres, Pharmaceutical Emulsions and Suspensions: 2nd Edition (Marcel Dekker, Inc, New York).

As used herein, the term food product refers to any food or feed suitable for consumption by humans or animals. The food product may be a prepared and packaged food (e.g., mayonnaise, salad dressing, bread, grain bar, beverage, etc.) or an animal feed (e.g., extruded and pelleted animal feed, coarse mixed feed or pet food composition). As used herein, the term foodstuff refers to any substance fit for human or animal consumption.

Food products or foodstuffs are for example beverages such as non-alcoholic and alcoholic drinks as well as liquid preparation to be added to drinking water and liquid food, non-alcoholic drinks are for instance soft drinks, sport drinks, fruit juices, such as for example orange juice, apple juice and grapefruit juice; lemonades, teas, near-water drinks and milk and other dairy drinks such as for example yoghurt drinks, and diet drinks. In another embodiment food products or foodstuffs refer to solid or semi-solid foods comprising the composition according to the invention. These forms can include, but are not limited to baked goods such as cakes and cookies, puddings, dairy products, confections, snack foods, or frozen confections or novelties (e.g., ice cream, milk shakes), prepared frozen meals, candy, snack products (e.g., chips), liquid food such as soups, spreads, sauces, salad dressings, prepared meat products, cheese, yogurt and any other fat or oil containing foods, and food ingredients (e.g., wheat flour).

Animal feed including pet food compositions advantageously include food intended to supply necessary dietary requirements, as well as treats (e.g., dog biscuits) or other food supplements. The animal feed comprising the composition according to the invention may be in the form of a dry composition (for example, kibble), semi-moist composition, wet composition, or any mixture thereof. Alternatively or additionally, the animal feed is a supplement, such as a gravy, drinking water, yogurt, powder, suspension, chew, treat (e.g., biscuits) or any other delivery form.

The term dietary supplement refers to a small amount of a compound for supplementation of a human or animal diet packaged in single or multiple dose units. Dietary supplements do not generally provide significant amounts of calories but may contain other micronutrients (e.g., vitamins or minerals). The term food products or foodstuffs also includes functional foods and prepared food products prepackaged for human consumption.

The term nutritional supplement refers to a composition comprising a dietary supplement in combination with a source of calories. In some embodiments, nutritional supplements are meal replacements or supplements (e.g., nutrient or energy bars or nutrient beverages or concentrates).

Dietary supplements of the present invention may be delivered in any suitable format. In preferred embodiments, dietary supplements are formulated for oral delivery. The ingredients of the dietary supplement of this invention are contained in acceptable excipients and/or carriers for oral consumption. The actual form of the carrier, and thus, the dietary supplement itself, is not critical. The carrier may be a liquid, gel, gelcap, capsule, powder, solid tablet (coated or noncoated), tea, or the like. The dietary supplement is preferably in the form of a tablet or capsule and most preferably in the form of a hard (shell) capsule. Suitable excipient and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). Preferred carriers include calcium carbonate, magnesium stearate, maltodextrin, and mixtures thereof. The various ingredients and the excipient and/or carrier are mixed and formed into the desired form using conventional techniques. The tablet or capsule of the present invention may be coated with an enteric coating that dissolves at a pH of about 6.0 to 7.0. A suitable enteric coating that dissolves in the small intestine but not in the stomach is cellulose acetate phthalate.

In other embodiments, the dietary supplement is provided as a powder or liquid suitable for adding by the consumer to a food or beverage. For example, in some embodiments, the dietary supplement can be administered to an individual in the form of a powder, for instance to be used by mixing into a beverage, or by stirring into a semi-solid food such as a pudding, topping, sauce, puree, cooked cereal, or salad dressing, for instance, or by otherwise adding to a food or the dietary supplement e.g. enclosed in caps of food or beverage container for release immediately before consumption. The dietary supplement may comprise one or more inert ingredients, especially if it is desirable to limit the number of calories added to the diet by the dietary supplement. For example, the dietary supplement of the present invention may also contain optional ingredients including, for example, herbs, vitamins, minerals, enhancers, colorants, sweeteners, flavorants, inert ingredients, and the like.

In some embodiments, the dietary supplements further comprise vitamins and minerals including, but not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin D3; cyanocobalamin; sodium selenite; copper sulfate; vitamin A; vitamin C; inositol; potassium iodide. Suitable dosages for vitamins and minerals may be obtained, for example, by consulting the U.S. RDA guidelines.

In other embodiments, the present invention provides nutritional supplements (e.g., energy bars or meal replacement bars or beverages) comprising the composition according to the invention. The nutritional supplement may serve as meal or snack replacement and generally provide nutrient calories. Preferably, the nutritional supplements provide carbohydrates, proteins, and fats in balanced amounts. The nutritional supplement can further comprise carbohydrate, simple, medium chain length, or polysaccharides, or a combination thereof. A simple sugar can be chosen for desirable organoleptic properties. Uncooked cornstarch is one example of a complex carbohydrate. If it is desired that it should maintain its high molecular weight structure, it should be included only in food formulations or portions thereof which are not cooked or heat processed since the heat will break down the complex carbohydrate into simple carbohydrates, wherein simple carbohydrates are monoor disaccharides. The nutritional supplement contains, in one embodiment, combinations of sources of carbohydrate of three levels of chain length (simple, medium and complex; e.g., sucrose, maltodextrins, and uncooked cornstarch).

Sources of protein to be incorporated into the nutritional supplement of the invention can be any suitable protein utilized in nutritional formulations and can include whey protein, whey protein concentrate, whey powder, egg, soy flour, soy milk soy protein, soy protein isolate, caseinate (e.g., sodium caseinate, sodium calcium caseinate, calcium caseinate, potassium caseinate), animal and vegetable protein and hydrolysates or mixtures thereof. When choosing a protein source, the biological value of the protein should be considered first, with the highest biological values being found in caseinate, whey, lactalbumin, egg albumin and whole egg proteins. In a preferred embodiment, the protein is a combination of whey protein concentrate and calcium caseinate. These proteins have high biological value; that is, they have a high proportion of the essential amino acids. See Modern Nutrition in Health and Disease, $8^{th}$ ed., Lea & Febiger, 1986, especially Volume 1, pages 30-32. The nutritional supplement can also contain other ingredients, such as one or a combination of other vitamins, minerals, antioxidants, fiber and other dietary supplements (e.g., protein, amino acids, choline, lecithin). Selection of one or several of these ingredients is a matter of formulation, design, consumer preferences and enduser. The amounts of these ingredients added to the dietary supplements of this invention are readily known to the skilled artisan. Guidance to such amounts can be provided by the U.S. RDA doses for children and adults. Further vitamins and minerals that can be added include, but are not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin D3; cyanocobalamin; sodium selenite; copper sulfate; vitamin A; vitamin C; inositol; potassium iodide.

The nutritional supplement can be provided in a variety of forms, and by a variety of production methods. In a preferred embodiment, to manufacture a food bar, the liquid ingredients are cooked; the dry ingredients are added with the liquid ingredients in a mixer and mixed until the dough phase is reached; the dough is put into an extruder, and extruded; the extruded dough is cut into appropriate lengths; and the product is cooled. The bars may contain other nutrients and fillers to enhance taste, in addition to the ingredients specifically listed herein.

It is understood by those of skill in the art that other ingredients can be added to those described herein, for example, fillers, emulsifiers, preservatives, etc. for the processing or manufacture of a nutritional supplement.

Additionally, flavors, coloring agents, spices, nuts and the like may be incorporated into the nutraceutical composition. Flavorings can be in the form of flavored extracts, volatile oils, chocolate flavorings, peanut butter flavoring, cookie crumbs, crisp rice, vanilla or any commercially available flavoring. Examples of useful flavoring include, but are not limited to, pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, walnut oil, cherry oil, cinnamon oil, clove oil, or peppermint oil; peanut butter, chocolate flavoring, vanilla cookie crumb, butterscotch or toffee. In one embodiment, the dietary supplement contains cocoa or chocolate.

Emulsifiers may be added for stability of the nutraceutical compositions. Examples of suitable emulsifiers include, but are not limited to, lecithin (e.g., from egg or soy), and/or mono and diglycerides. Other emulsifiers are readily apparent to the skilled artisan and selection of suitable emulsifier(s) will depend, in part, upon the formulation and final product. Preservatives may also be added to the nutritional supplement to extend product shelf life. Preferably, preservatives such as potassium sorbate, sodium sorbate, potassium benzoate, sodium benzoate or calcium disodium EDTA are used.

In addition to the carbohydrates described above, the nutraceutical composition can contain natural or artificial (preferably low calorie) sweeteners, e.g., saccharides, cyclamates, aspartamine, aspartame, acesulfame K, and/or sorbitol. Such artificial sweeteners can be desirable if the nutritional supplement is intended to be consumed by an overweight or obese individual, or an individual with type II diabetes who is prone to hyperglycemia.

Moreover, a multi-vitamin and mineral supplement may be added to the nutraceutical compositions of the present invention to obtain an adequate amount of an essential nutrient, which is missing in some diets. The multi-vitamin and mineral supplement may also be useful for disease prevention and protection against nutritional losses and deficiencies due to lifestyle patterns.

The dosage and ratios of catechin and/or epicatechin and additional components administered via a nutraceutical will vary depending upon known factors, such as the physiological characteristics of the particular composition and its mode and route of administration; the age, health and weight of the recipient; the nature and extent of the symptoms; the kind of concurrent treatment; the frequency of treatment; and the effect desired which can determined by the expert in the field with normal trials, or with the usual considerations regarding the formulation of a nutraceutical composition.

It will be understood, however, that the specific dose level for any particular patient will depend on a variety of factors including the activity of the specific compound employed, the age, body weight, general health, sex and diet of the individual being treated; the time and route of administration; the rate of excretion; other drugs which have previously been administered; and the severity of the particular disease undergoing therapy, as is well understood by those skilled in the art.

Examples of each mechanism for preventing or treating drug-associated perturbation of mitochondrial function or structure via the use of the claimed agents include the following:

Modulation of Mitochondrial Metabolism

Diabetes, defined as potentially toxic hyperglycemia, is a known complication of the administration of cortisol, prednisone, or methyl prednisolone (corticosteroids), affecting up to 50% of patients receiving them, and limiting both the dose and duration of treatment with corticosteroids. Corticosteroids can induce pyruvate dehydrogenase kinase-4 (PDK-4) as an effect unrelated to their principal therapeutic effect as anti-inflammatory agents. PDK-4 can phosphorylate pyruvate dehydrogenase (PD) inhibiting its function. PD is a mitochondrial enzyme, the first in a process that contributes to transforming pyruvate into acetyl-CoA which is then used in the citric acid cycle within the mitochondria to carry out cellular respiration. Pyruvate derives from the breakdown of glucose within the cytoplasm, whence it is transported into the mitochondria. As pyruvate metabolism within the mitochondria is slowed by the presence of corticosteroids, cells stop taking up glucose, which then accumulates in the circulation, causing hyperglycemia. Other agents known to activate PDK-4 and inhibit PD include the fibrates, such as clofibrate, ciprofibrate, and bexafibrate. Such drugs when combined with corticosteroids may exacerbate the severity of diabetes as an adverse event experienced by the patient. In another example of consequences of PDK-4 upregulation, when the metabolism of glucose is blocked, the mitochondria attempt to oxidize fat as a fuel source which requires degradation of intracellular triglycerides. If there is not sufficient triglyceride, either because the subject has little body fat or because of triglyceride inhibitors such as the fibrates, mitochondria then turn to metabolism of an amino acid glutamine. Glutamine must be derived from catabolism of muscle fiber proteins resulting in muscle weakness, or myopathy, another frequent complication of corticosteroid treatment. Epicatechin and other agents cited herein prevents or reverses the hyperglycemia of corticosteroids by stimulating mitochondrial respiration via the enhanced uptake of pyruvate into the mitochondria.

Drug Associated Mitochondrial Injury

Mitochondrial injury can be induced by exposure of mitochondria to increased intracellular calcium, increased reactive oxygen radicals generated in the cytoplasm or within the mitochondria themselves, intracellular ATP depletion, or impaired access to oxygen. Each of these factors can induce the formation of mitochondrial permeability transition pores by aggregating proteins within the mitochondrial membrane. Such pores connect the inner mitochondrial membrane with the outer mitochondrial membrane, causing a non-selective flux of ions and water between the inner mitochondria and the cytoplasm beyond (e.g., organelle swelling). Initially such pores prevent ATP synthesis by preventing the formation of an electrical potential across the mitochondrial inner membrane, potential which is necessary for the synthesis of ATP. If sufficient pores remain in place for a sustained period, the mitochondria progress to irreversible involution and permanent nonfunction, and are then expelled from the cell as debris. Failing mitochondria release cytochrome c, an apoptosis-inducing agent that activates intracellular proteases, such as caspases, that lead to the death of the cell harboring the damaged mitochondria.

Inotropes are a widely used class of drugs in congestive heart failure that are used to augment myocardial contractility via increased intracellular calcium. Adverse consequences of prolonged inotrope use include ischemia, arrythmias, and death. Prolonged increases in intracellular calcium are associated with increased mitochondrial permeability pore formation. Other medicines can cause toxic increases of intracellular calcium by other mechanisms, such as changes in ion channel activity in both the plasma membrane and the sarcoplamic reticulum. These drugs include chemotherapeutics such as doxyrubicin, statins, and corticosteroids. As is the case with hyperglycemia, the corticosteroids most injurious of mitochondrial function and structure are prednisolone, triamcinalone, dexamethasone, and beclamethasone. The mitochondrial toxic effects of these drugs can be more severe if the patient is on two or more of such compounds to treat underlying conditions.

As described herein, epicatechin prevents mitochondrial pore formation in response to calcium and prevents inotrope-associated cardiac toxicity. Nicorandil has been shown to prevent mitochondrial pore formation in response to ischemia, but has not been studied with respect to its effects on drug-associated toxicity.

Sustained Mitochondrial Depletion

The chronic presence within the body of drugs which injure mitochondria can result in a state of transition from reversible mitochondrial injury to irreversible mitochondrial injury, failure of the mitochondria, and dysfunction or death of the cells harboring those mitochondria. In one example, persistently elevated intracellular calcium in the setting of an inotrope or corticosteroid therapy can result in mitochondrial pore formation, failure of the mitochondria, and release of cytochrome c. In another example, chronic exposure of patients to statins is associated with loss of mitochondrial coenzyme Q, a critically important mitochondrial protein necessary for electron transport and thus oxidative phosphorylation that also serves as an effective anti-oxidant protecting against damage to the mitochondria by oxygen radicals. Persistent loss of coenzyme Q is associated with release of cytochrome c by the failed mitochondria and consequent death of the cell. In another example, anti-viral drugs, such as nucleo(t)side analogs such as ziduvidine and chemotherapeutics capable of alkylating or intercalating into DNA can damage mitochondrial DNA and cause permanent injury to, or depletion of, mitochondria. The presence of more than one drug toxic to the mitochondria can increase the rate and severity of chronic mitochondrial depletion or dysfunction. The presence of conditions or illnesses associated with loss of mitochondria, such as diabetes, obesity, and aging, can increase the potential for drug-associated mitochondrial toxicity.

The consequences of chronic perturbation of mitochondria function or structure include chronic myopathy, sarcopenia, persistent diabetes, chronic fatigue syndromes, gastrointestinal symptoms, liver, and cardiovascular dysfunction and failure, neurological symptoms, impaired sleep, and persistent alteration in cognitive acuity or function, such as memory.

What is needed to provide a therapeutic response to a state of chronic perturbation of mitochondrial structure or function is an agent or agents that can induce the synthesis of new mitochondria or additional mitochondrial proteins (e.g., cristae or mitochondrial complex proteins) within each mitochondrion, termed mitochondrial biogenesis. However, the only known effective stimulator of mitochondrial biogenesis is exercise. The ability of exercise to induce biogenesis is rapidly lost with aging. The capacity for mitochondrial biogenesis is also lost in the setting of several underlying diseases including aging, diabetes, and obesity. What is needed is an agent that stimulates the synthesis on new mitochondrial proteins or new mitochondria to replace the mitochondria lost as a result of acute or chronic perturbation of mitochondrial function and structure secondary to drug toxicity. An agent that stimulates mitochondrial biogenesis when drugs that perturb mitochondrial function or structure are administered to a patient in the state of a condition or illness that is already associated with mitochondrial depletion, such as aging, diabetes, or obesity, is particularly needed.

As an example of a therapeutic agent, epicatechin can stimulate mitochondrial protein synthesis in human skeletal muscle cells in culture. As another example, epicatechin can stimulate mitochondrial biogenesis in the aging mouse, with a consequent improvement in muscle function and endurance.

EXAMPLES

Example 1

FIG. 1 depicts epicatechin stimulation on-demand mitochondrial respiration in human cells. In cultures of differentiated human skeletal muscle cells treated with 100 nM epicatechin ("Epi") for 48 h maximal rates of respiration (elicited by addition of the chemical uncoupler FCCP) were profoundly increased (top panel) in a manner that is dose dependent (bottom panel). Rates of respiration are reported as oxygen consumption rates (OCR) and were measured using a Seahorse apparatus.

Example 2

Figure 2:
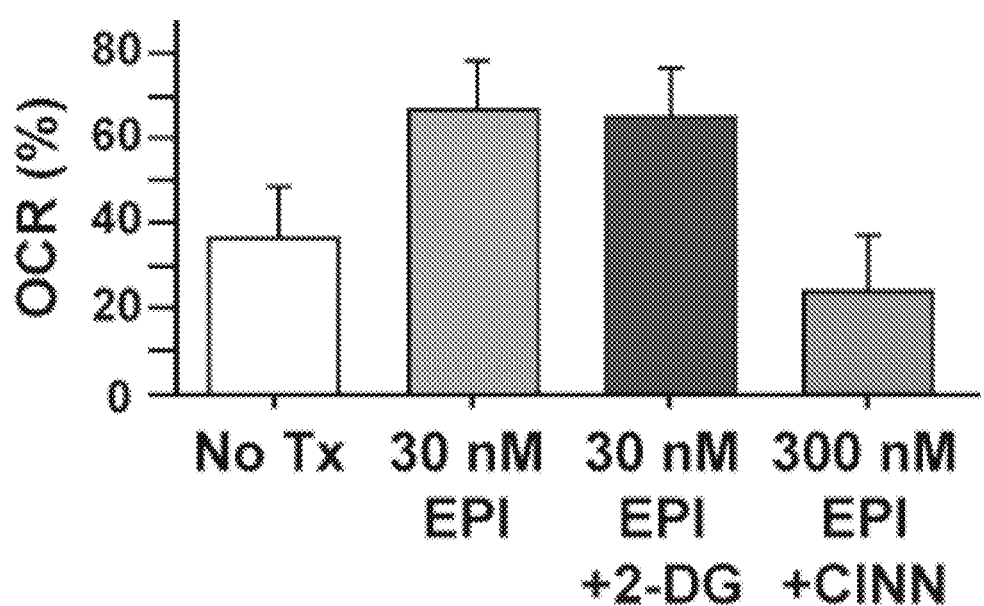
FIG. 2 depicts blockade of epicatechin's stimulatory effect by an inhibitor of pyruvate transport.

FIG. 2 depicts blockade of epicatechin's stimulatory effect by an inhibitor of pyruvate transport. Cultures of differentiated human skeletal muscle cells were treated with 30 nM epicatechin (EPI) for 48 h, and maximal rates of respiration were blocked by an inhibitor of pyruvate transport into mitochondria (a-cyannocinnamate=CINN) but not by deoxyglucose (2-DG). These data support epicatechin's stimulation of mitochondrial respiration by enhanced pyruvate transport into mitochondria.

Example 3

Figure 3:
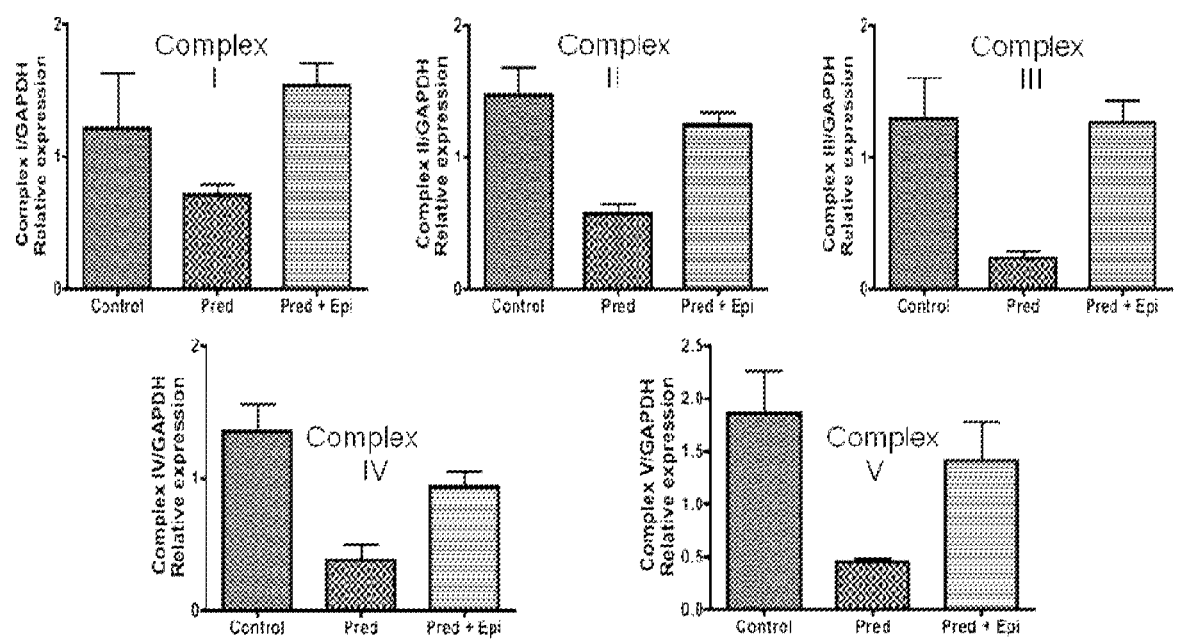
FIG. 3 depicts the effects of the administration of 10 consecutive days of prednisolone on rat skeletal muscle mitochondrial oxidative phosphorylation related complexes levels.

FIG. 3 depicts the effects of the administration of 10 consecutive days of prednisolone (10 mg/kg/day, SC) on rat skeletal muscle mitochondrial oxidative phosphorylation (OXPHOS) related complexes levels as assessed by Western blots. Three groups of male rats were analyzed: 1) control group (saline solution, SC and saline solution by gavage BID); 2) prednisolone (10 mg/kg/day, SC and saline solution by gavage BID); and 3) prednisolone (10 mg/kg/day, SC) plus epicatechin (Epi; 1 mg/kg/day by gavage BID). Western blots of isolated skeletal muscle (quadriceps) from each group were probed with a cocktail of monoclonal antibodies to electron transport chain proteins (OXPHOS) (20 KDa subunit of complex I, 26 KDa subunit of complex IV, subunit core 2 of complex III, 30 KDa complex II and ATP synthase 54 Kda complex V). Mitochondrial complex (I-V) levels were reduced with prednisolone treatment (mitochondrial damage). Epicatechin reverses prednisolone deleterious effects.

Western blots were performed as follows: Approximately 50 mg of the heart and quadriceps femoris muscles were homogenized with a polytron in 500 μl lysis buffer (1% triton X-100, 20 mM Tris, 140 mM NaCl, 2 mM EDTA, and 0.1% SDS) with protease and phosphatase inhibitor cocktails (P2714 and P2850, Sigma-Aldrich, St. Louis, Mo.) supplemented with 0.15 mM PMSF, 5 mM Na3VO4 and 3 mM NaF. Homogenates were passed through an insulin syringe five times, sonicated for 30 min at 4° C. and centrifuged (12,000 g) for 10 min. The total protein content was measured in the supernatant using the Bradford method. A total of 40 μg of protein was loaded onto a 4%-15% precast TGX polyacrylamide gel (Bio-rad), electrotransferred (12 V, 50 minutes), incubated for 1 h in blocking solution (5% nonfat dry milk in TBS plus 0.1% Tween 20 [TBS-T]), followed by a 3-h incubation at room temperature with primary mouse(−)-Epicatechin and muscular fatigue 10 monoclonal antibodies. MitoProfile (Total OXPHOS from MitoSciences), Porin (Cell Signaling), and mitofilin (Cell Signaling) primary antibodies were diluted 1:1000 and GAPDH (rabbit polyclonal, Cell Signaling) primary antibody was diluted 1:2000 in TBS-T plus 5% nonfat dry milk. Membranes were washed (3× for 5 min) in TBS-T and incubated 1 h at room temperature in the presence of HRP-conjugated secondary antibodies (Cell Signaling) diluted 1:10,000 in blocking solution. Membranes were again washed 3 times in TBS-T, and the immunoblots were developed using an ECL Plus detection kit (Amersham-GE). The band intensities were digitally quantified using ImageJ software. As depicted, when epicatechin is added to the cell culture medium, mitochondrial complex levels are improved (FIG. 3).

Example 5

Figure 4:
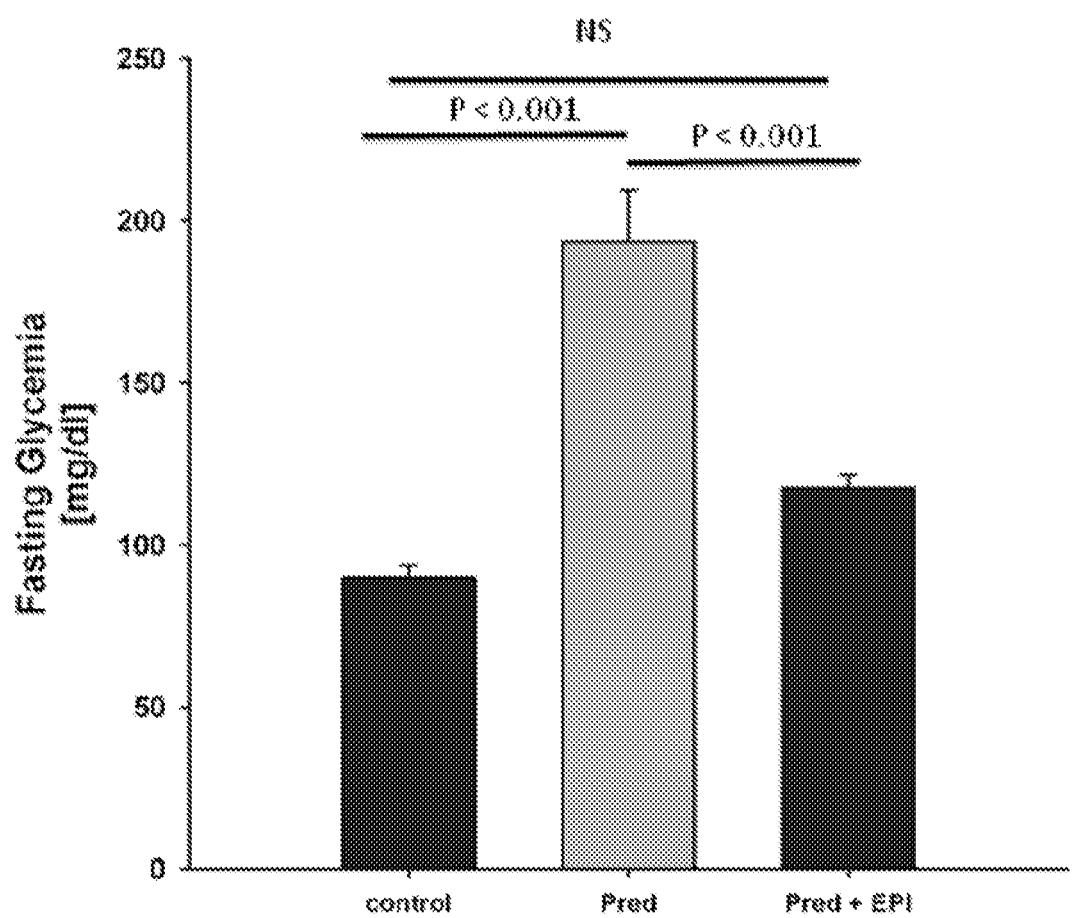
FIG. 4 depicts the effects of the administration of 10 consecutive days of prednisolone on glucose levels.

FIG. 4 depicts the effects of the administration of 10 consecutive days of prednisolone (10 mg/kg/day, SC) on glucose levels. Three groups of male rats were analyzed: 1) control group (saline solution, SC and saline solution by gavage BID); 2) prednisolone (10 mg/kg/day, SC and saline solution by gavage BID) and; 3) prednisolone (10 mg/kg/day, SC) plus epicatechin (Epi; 1 mg/kg/day by gavage BID).

Blood samples were obtained from animals on each group after 12 hours fasting, Glucose levels were determined spectrophotometrically with an autokit glucose (Wako) kit. Animals receiving corticosteroid only displayed significant hyperglycemia, those also receiving epicatechin exhibited a marked improvement in their hyperglycemia. (FIG. 4).

Example 6

Figure 5:
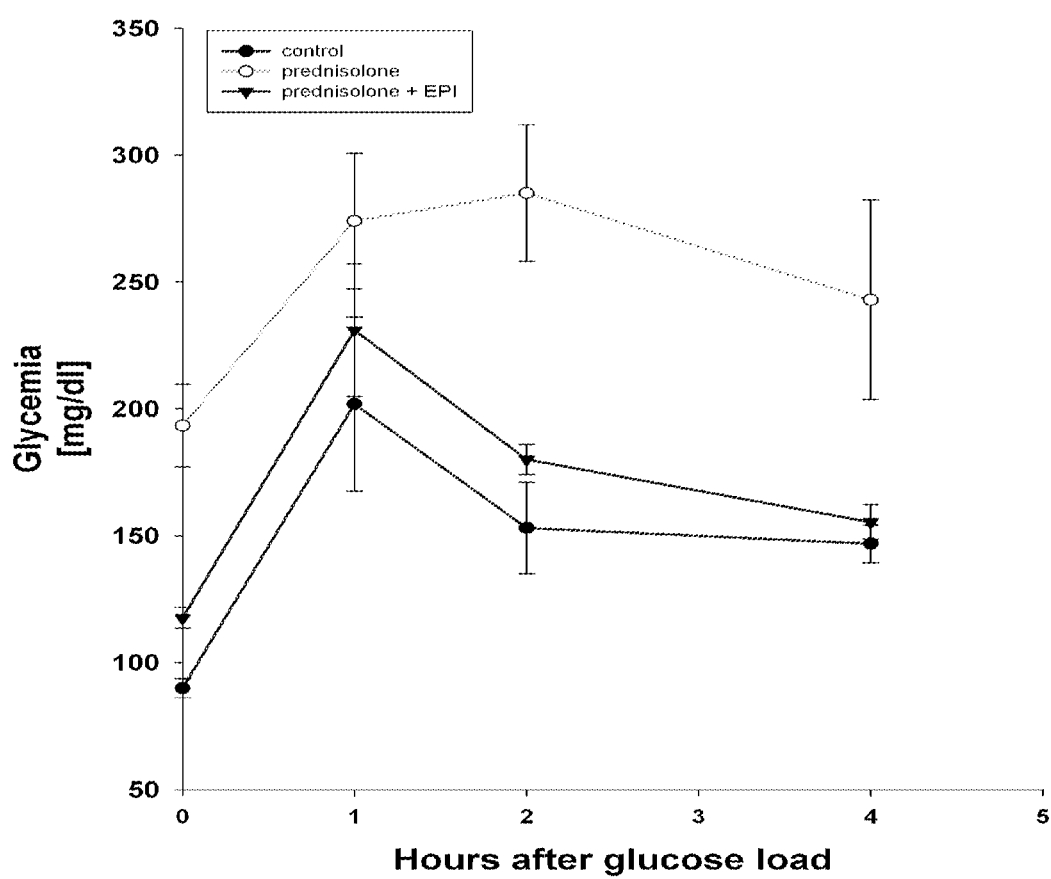
FIG. 5 depicts the effects of the administration of 10 consecutive days of prednisolone on an oral glucose tolerance test.

FIG. 5 depicts the effects of the administration of 10 consecutive days of prednisolone (10 mg/kg/day, SC) on an oral glucose tolerance test. Three groups of male rats were analyzed: 1) control group (saline solution, SC and saline solution by gavage BID); 2) prednisolone (10 mg/kg/day, SC and saline solution by gavage BID) and; 3) prednisolone (10 mg/kg/day, SC) plus epicatechin (Epi; 1 mg/kg/day by gavage BID).

Blood samples were obtained from animals on each group from 0-4 hours after an oral glucose charge (1.25 g/Kg). Glucose levels were determined spectrophotometrically with an autokit glucose (Wako) kit. Abnormal glucose tolerance, indicating insulin resistance associated with corticosteroid therapy, is largely reversed by combining epicatechin with prednisolone (FIG. 5).

Example 7

Figure 6:
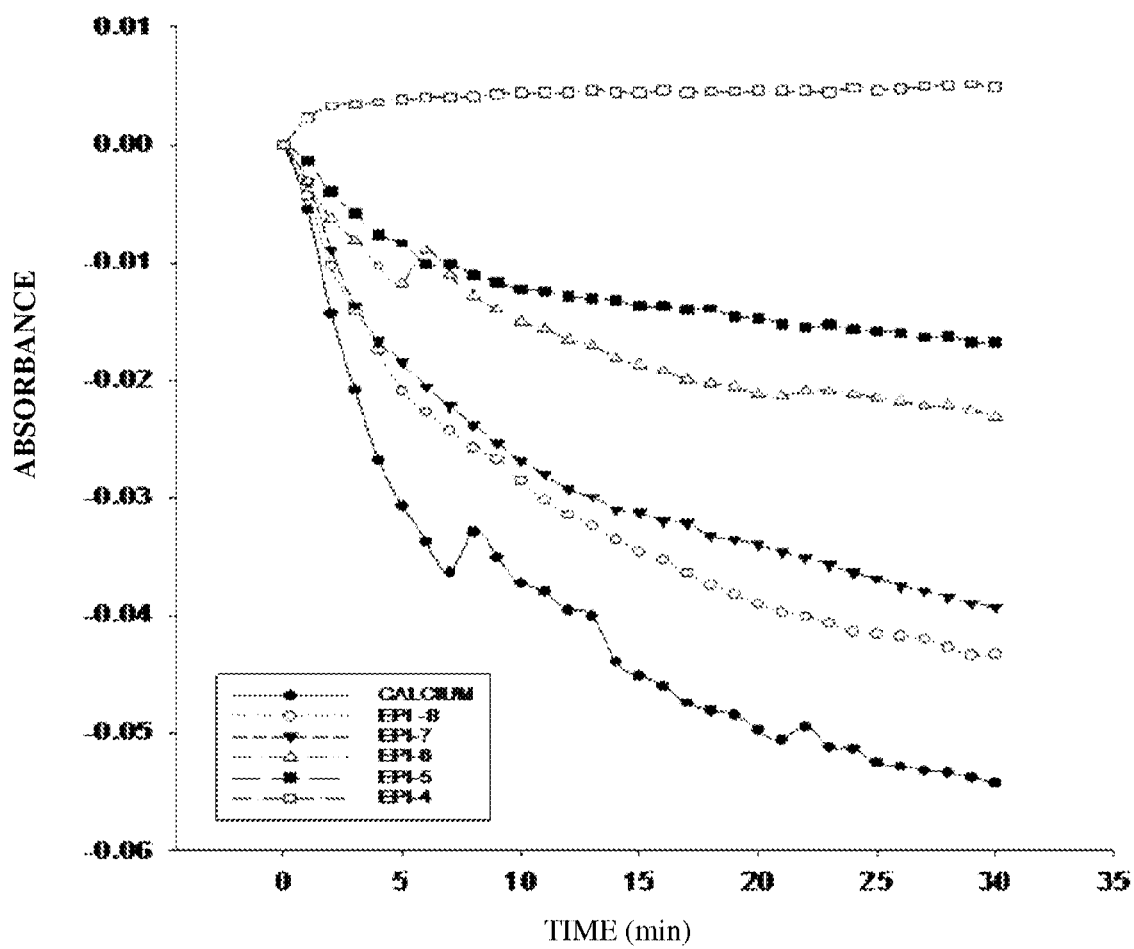
FIG. 6 depicts the protective effect of epicatechin on calcium induced mitochondrial damage as assessed by mitochondrial swelling.

FIG. 6 depicts the protective effect of epicatechin on calcium induced mitochondrial damage (as measured by mitochondrial swelling). Swelling was evaluated by monitoring changes in optical density (OD, light absorbance) as follows: Hearts from male rats were excised and weighed. Left ventricles were homogenized (0.1 g/mL) in solution A (Sucrose 2M, EDTA 0.01M, Hepes 0.5M: pH=7.4), centrifuged 10 min (800×g), 4° C., the supernatant was centrifuged 10 min (8000×g), 4° C. and the pellet was re-suspended in solution B (Sucrose 2M, EDTA 0.01M, Tris 0.5M-H2PO4-50 mM: pH=7.4) and centrifuged 10 min (10000×g), 4° C. Pellet was re-suspended in 10 mL of solution C (Sucrose 2M, EDTA 0.01M, Tris 0.5M-H2PO4-50 mM, Succinate 1M: pH=7.4. 33 μM of CaCl2 was then, added in order to induce mitochondrial damage (swelling measured through OD changes at 535 nm, monitored continuously during 30 min. Epicatechin ($10^{-8}$-$10^{-4}$ M) blocks in a dose dependent manner the swelling effects of calcium in isolated mitochondria.

Example 8

Figure 7:
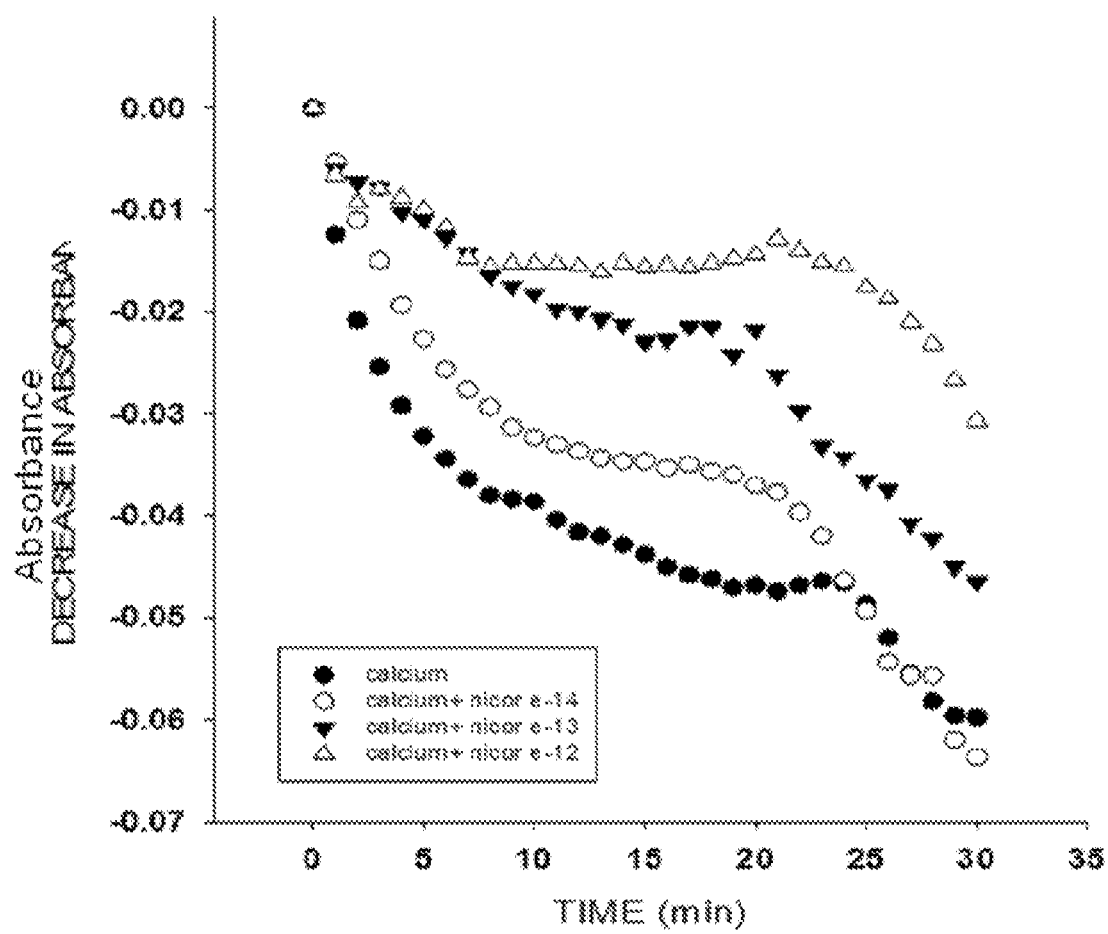
FIG. 7 depicts the protective effect of nicorandil on calcium induced mitochondrial damage as assessed by mitochondrial swelling.

FIG. 7 depicts the protective effect of nicorandil on calcium induced mitochondrial damage (swelling). Hearts from male rats were excised and weighed. Left ventricles were homogenized (0.1 g/mL) in solution A (Sucrose 2M, EDTA 0.01M, Hepes 0.5M: pH=7.4), centrifuged 10 min (800×g), 4° C., the supernatant was centrifuged 10 min (8000×g), 4° C. and the pellet was re-suspended in solution B (Sucrose 2M, EDTA 0.01M, Tris 0.5M-H2PO4-50 mM: pH=7.4) and centrifuged 10 min (10000×g), 4° C. Pellet was re-suspended in 10 mL of solution C (Sucrose 2M, EDTA 0.01M, Tris 0.5M-H2PO4-50 mM, Succinate 1M: pH=7.4. 33 μM of CaCl2 was then, added in order to induce mitochondrial damage (swelling measured through OD changes at 535 nm, monitored continuously during 30 mM. Nicorandil ($10^{-14}$-$10^{-12}$ M) blocks in a dose dependent manner the swelling effects of calcium in isolated mitochondria Example 9

Figure 8:
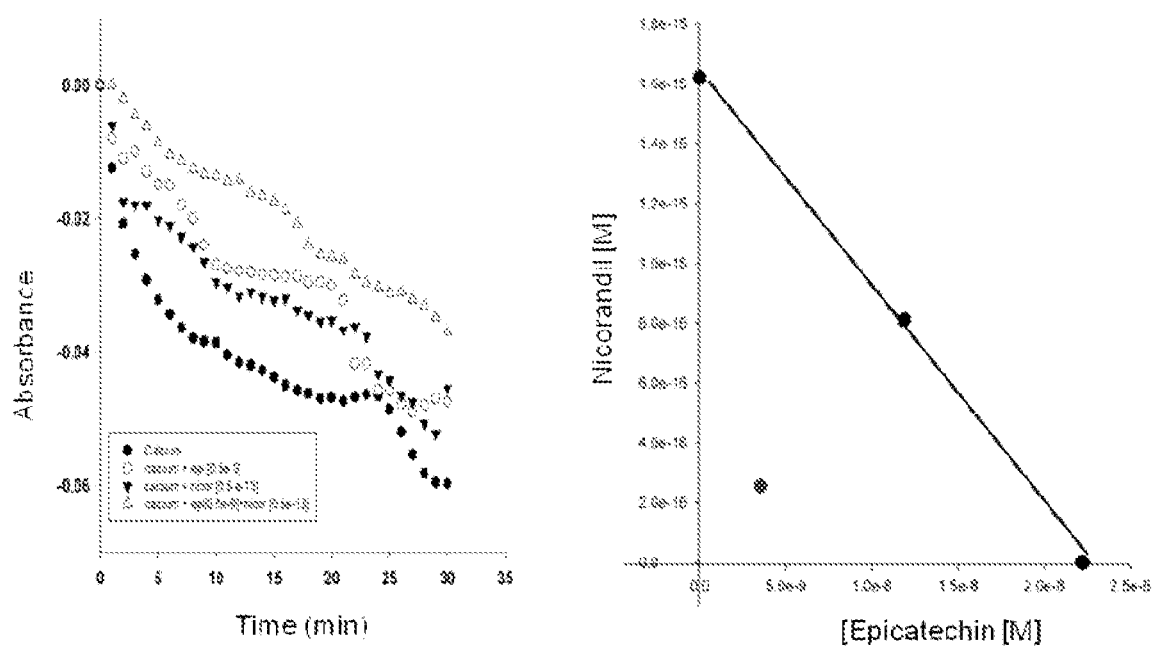
FIG. 8 depicts the combined effects of epicatechin and nicorandil on calcium induced mitochondrial damage as assessed by mitochondrial swelling.

FIG. 8 depicts the combined effects of Epicatechin and Nicorandil on calcium induced mitochondrial damage (swelling). Hearts from male rats were excised and weighed. Left ventricles were homogenized (0.1 g/mL) in solution A (Sucrose 2M, EDTA 0.01M, HEPES 0.5M: pH=7.4), centrifuged 10 min (800×g), 4° C., the supernatant was centrifuged 10 min (8000×g), 4° C. and the pellet was re-suspended in solution B (Sucrose 2M, EDTA 0.01M, Tris 0.5M-H2PO4-50 mM: pH=7.4) and centrifuged 10 min (10000×g), 4° C. Pellet was re-suspended in 10 mL of solution C (Sucrose 2M, EDTA 0.01M, Tris 0.5M, H2PO4 50 mM, Succinate 1M: pH=7.4). 33 μM of CaCl2 was then added in order to induce mitochondrial damage (swelling measured through absorbance changes at 535 nm, monitored continuously during 30 min.

Dose-response effects on mitochondrial swelling to EPI and NICO treatment were pursued. The effective dose (ED) at 30, 40 and 50% of maximal effect were determined by using Michaelis-Menten (M-N) and probabilistic (Probits) analysis. The ED40 of EPI and Doxy was determined and isobolografic analysis of the combined doses of EPI and Doxy performed to evaluate any synergistic effect of the combination treatment. As depicted in FIG. 8, right panel (as noted by the data point which falls below a predicted additive line), a synergistic effect of Epicatechin and Nicorandil was observed.

Example 10

Figure 9:
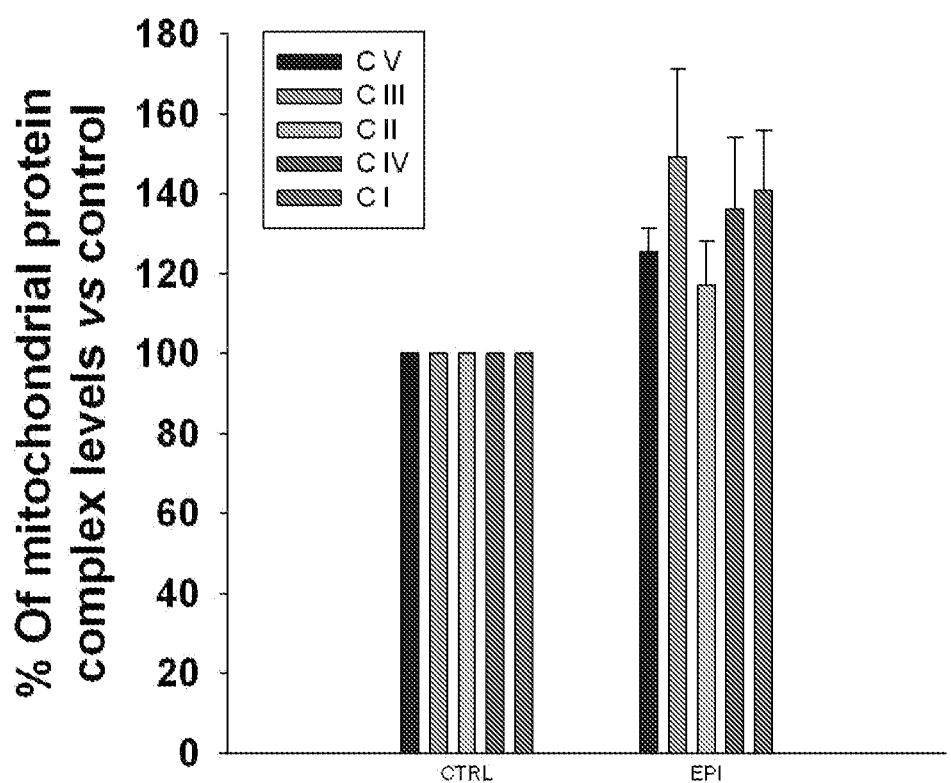
FIG. 9 depicts changes in oxidative phosphorylation-related complexes expression in human coronary artery endothelial cells after incubation with epicatechin.

FIG. 9 depicts changes in oxidative phosphorylation (OXPHOS)-related complexes expression in Human Coronary Artery Endothelial cells (HCAEC) after incubation with [1 µM] Epic atechin during 48 h.

Western blots were performed as follows: Approximately 50 mg of the heart and quadriceps femoris muscles were homogenized with a polytron in 500 µL lysis buffer (1% triton X-100, 20 mM Tris, 140 mM NaCl, 2 mM EDTA, and 0.1% SDS) with protease and phosphatase inhibitor cocktails (P2714 and P2850, Sigma-Aldrich, St. Louis, Mo.) supplemented with 0.15 mM PMSF, 5 mM Na3VO4 and 3 mM NaF. Homogenates were passed through an insulin syringe five times, sonicated for 30 min at 4° C. and centrifuged (12,000 g) for 10 min. The total protein content was measured in the supernatant using the Bradford method. A total of 40 µg of protein was loaded onto a 4%-15% precast TGX polyacrylamide gel (Bio-rad), electrotransferred (12 V, 50 minutes), incubated for 1 h in blocking solution (5% nonfat dry milk in TBS plus 0.1% Tween 20 [TBS-T]). HCAEC were probed with a cocktail of monoclonal antibodies to electron transport chain proteins (OXPHOS) (20 KDa subunit of complex I, 26 KDa subunit of complex IV, subunit core 2 of complex III, 30 Kda complex II and ATP synthase 54 Kda complex V). MitoProfile (Total OXPHOS from MitoSciences), Porin (Cell Signaling), and mitofilin (Cell Signaling) primary antibodies were diluted 1:1000 and GAPDH (rabbit polyclonal, Cell Signaling) primary antibody was diluted 1:2000 in TBS-T plus 5% nonfat dry milk. Membranes were washed (3× for 5 min) in TBS-T and incubated 1 h at room temperature in the presence of HRP-conjugated secondary antibodies (Cell Signaling) diluted 1:10,000 in blocking solution. Membranes were again washed 3 times in TBS-T, and the immunoblots were developed using an ECL Plus detection kit (Amersham-GE). The band intensities were digitally quantified using ImageJ software. A significant increase in the expression of all complexes was found with epi treatment.

Example 11

Figure 10:
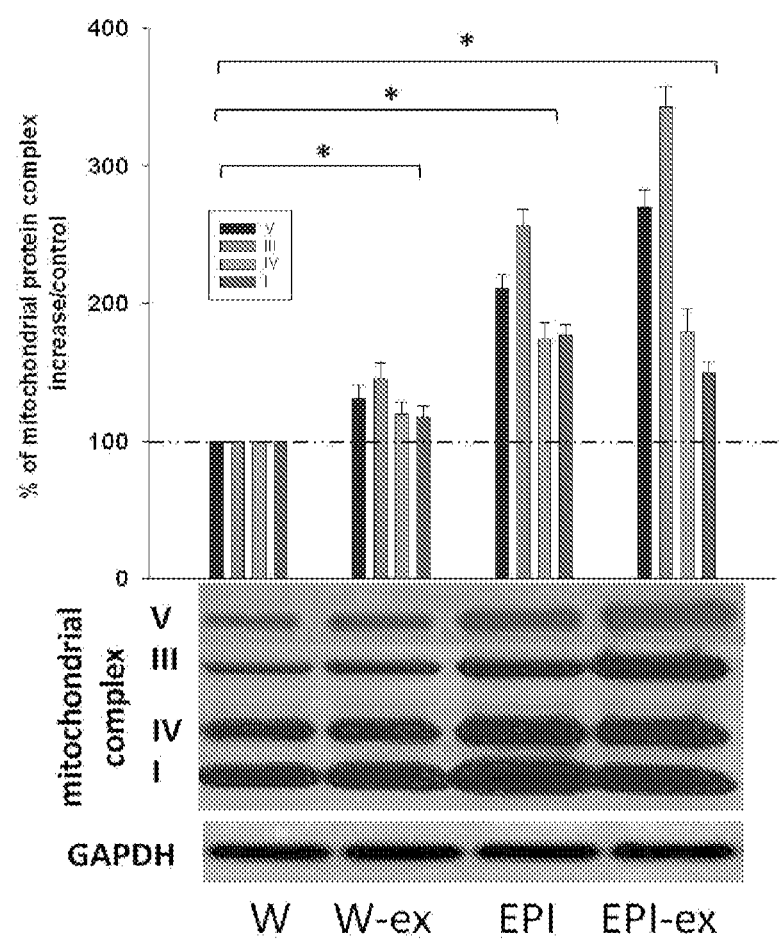
FIG. 10 further depicts the effect of epicatechin administration on mitochondrial protein levels.

FIG. 10 further elucidates the effect of epicatechin on mitochondrial protein levels. Twenty-seven older, male mice (12-months old) were separated into four groups: 1) (−)-epicatechin only; 2) (−)-epicatechin with endurance training; 3) water; and 4) water with endurance training. Water was used as the placebo, because it was the solution used to dissolve (−)-epicatechin. The endurance training regimen consisted of 5×/week at 30 minutes per session at a moderate intensity on a rodent treadmill during the 15 day study period. On at least two occasions prior to the test all mice were familiarized with the treadmill (model CL-4, Omnitech, Columbus, Ohio) at a slow speed (5 m/min) at 10° incline for approximately 5-10 minutes. The incremental test consisted of warm-up at 4 m/min for two minutes followed by an increase of 2 m/min every minute thereafter. A shock grid (0.2 milliamps) and air jets at the back of the treadmill were used to discourage the mice from stopping while the treadmill belt was moving. Exhaustion was determined when the mouse was no longer able to maintain its normal running position(−)-Epicatechin and muscular fatigue on the treadmill and/or was unwilling to run as indicated by the frequent contact (i.e., touching the shock grid with each stride) or sitting on the shock grid. The running time was measured and running distance. Exercise Intervention For 15 days, mice in groups 2 and 4 underwent treadmill training which began at approximately 14 m/min (50% of maximal treadmill speed) at 10° incline for 30-minutes five times per week Western blots of isolated skeletal muscle (isolated quadriceps after 48 hours of treadmill) from each group were probed with a cocktail of monoclonal antibodies to electron transport chain proteins (OXPHOS) (20 KDa subunit of complex I, 26 KDa subunit of complex IV, subunit core 2 of complex III, 30 Kda complex II and ATP synthase 54 KDa complex V). As shown, epicatechin (1 mg/kg/day BID for 15 days) stimulates increases in mitochondrial complex proteins in the aging (1 year old) mouse. The effects are greater than those generated by exercise alone and can become additive when combined. Groups shown are control (water=W), exercise only (W-ex), epicatechin (EPI) and epicatechin+exercise (EPI-ex).

Example 12

Figure 11:
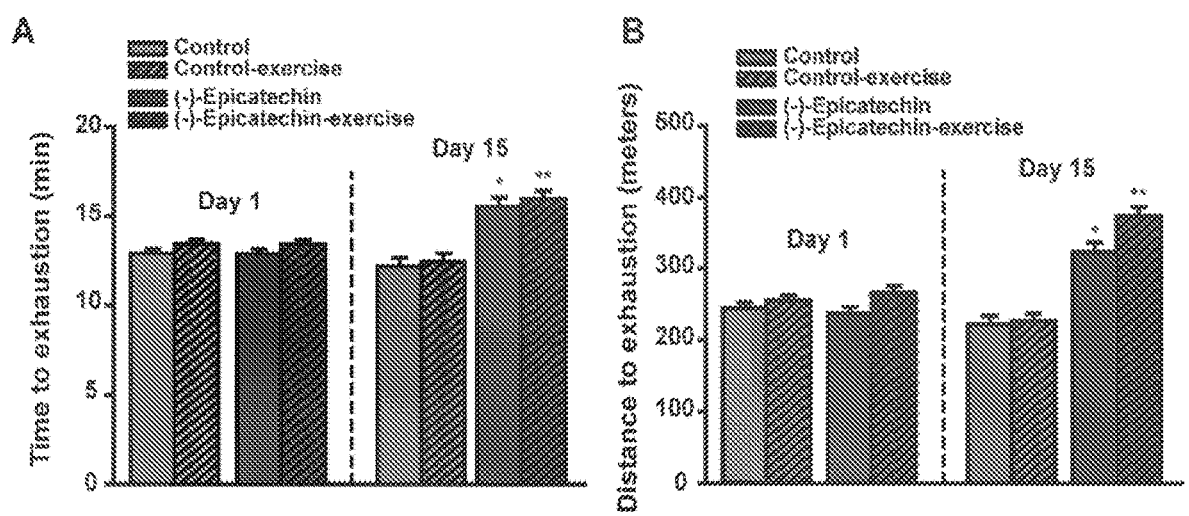
FIG. 11 depicts the effect of epicatechin on treadmill performance in the aging mouse.

FIG. 11 depicts the ability of Epicatechin (1 mg/kg/day BID for 15 days) to enhance treadmill performance in the aging mouse. Twenty-seven older, male mice (12-months old) were separated into four groups: 1) (−)-epicatechin only; 2) (−)-epicatechin with endurance training; 3) water; and 4) water with endurance training. Water was used as the placebo, because it was the solution used to dissolve (−)-epicatechin. The endurance training regimen consisted of 5×/week at 30 minutes per session at a moderate intensity on a rodent treadmill during the 15 day study period. On at least two occasions prior to the test all mice were familiarized with the treadmill (model CL-4, Omnitech, Columbus, Ohio) at a slow speed (5 m/min) at 10° incline for approximately 5-10 minutes. The incremental test consisted of warm-up at 4 m/min for two minutes followed by an increase of 2 m/min every minute thereafter. A shock grid (0.2 milliamps) and air jets at the back of the treadmill were used to discourage the mice from stopping while the treadmill belt was moving. Exhaustion was determined when the mouse was no longer able to maintain its normal running position (−)-Epicatechin and muscular fatigue on the treadmill and/or was unwilling to run as indicated by the frequent contact (i.e., touching the shock grid with each stride) or sitting on the shock grid. The running time was measured and running distance. Exercise Intervention For 15 days, mice in groups 2 and 4 underwent treadmill training which began at approximately 14 m/min (50% of maximal treadmill speed) at 10° incline for 30-minutes five times per week The changes in incremental treadmill performance prior to- and following 15 days of treatment with (−)-epicatechin were significantly ($p<0.001$) different between pre- and 15-day post treatment for both (−)-epicatechin groups for speed (meters per minute) and time, whereas no significant differences ($p>0.05$) were found pre- to post-treatment for the two water groups.

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

What is claimed is:

1. A method for treating decreased mitochondrial number and/or function in a subject, the method comprising administering an effective amount of epicatechin or epicatechin prodrug that is at least 90% pure relative to epicatechin derivatives, catechin and catechin derivatives, to the subject.

2. The method of claim 1, wherein the epicatechin or epicatechin prodrug is administered at a dosage between 0.1 mg/kg and 10 mg/kg.

3. A method for ameliorating mitochondrial toxicity in a subject induced by a drug, the method comprising administering an effective amount of epicatechin or epicatechin prodrug that is at least 90% pure relative to epicatechin derivatives, catechin and catechin derivatives, to the subject.

4. The method of claim 3, wherein the drug and the epicatechin or epicatechin prodrug are administered together.

5. The method of claim 3, wherein the epicatechin or epicatechin prodrug is administered at a dosage between 0.1 mg/kg and 10 mg/kg.

6. The method of claim 3, wherein the drug is selected from the group consisting of: a. a corticosteroid; b. metformin or phenformin; c. a thiozolidinedione; d. a statin; e. ibuprofen, celecoxib, diclofenac, indomethacin, mefenamic acid, meloxicam, naproxen, or piroxicam, f. a fibrate g. a chemotherapeutic; and h. an antipsychotic.

7. A method for treating mitochondrial depletion induced by a drug whose side effects are associated with perturbation of mitochondrial number, function or structure in a subject, the method comprising administering an effective amount of epicatechin or epicatechin prodrug that is at least 90% pure relative to epicatechin derivatives, catechin and catechin derivatives, to the subject.

8. The method of claim 7, wherein the epicatechin or epicatechin prodrug is administered at a dosage between 0.1 mg/kg and 10 mg/kg.

9. The method of claim 1, wherein the decreased mitochondrial number and/or function is associated with diabetes in the subject.

10. The method of claim 9, wherein the epicatechin or epicatechin prodrug is administered at a dosage between 0.1 mg/kg and 10 mg/kg.

11. The method of claim 1, wherein the decreased mitochondrial number and/or function is associated with aging in the subject.

12. The method of claim 11, wherein the epicatechin or epicatechin prodrug is administered at a dosage between 0.1 mg/kg and 10 mg/kg.

13. The method of claim 1, wherein the decreased mitochondrial number and/or function is associated with obesity in the subject.

14. The method of claim 13, wherein the epicatechin or epicatechin prodrug is administered at a dosage between 0.1 mg/kg and 10 mg/kg.

* * * * *